United States Patent
Akashi et al.

(10) Patent No.: US 12,307,455 B2
(45) Date of Patent: May 20, 2025

(54) EVALUATION SYSTEM, EVALUATION METHOD, PROGRAM, SERVER DEVICE, AND TERMINAL DEVICE

(71) Applicant: Panasonic Intellectual Property Management Co., Ltd., Osaka (JP)

(72) Inventors: Yosuke Akashi, Osaka (JP); Kengo Abe, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 622 days.

(21) Appl. No.: 17/631,874

(22) PCT Filed: Jul. 13, 2020

(86) PCT No.: PCT/JP2020/027232
§ 371 (c)(1),
(2) Date: Jan. 31, 2022

(87) PCT Pub. No.: WO2021/020090
PCT Pub. Date: Feb. 4, 2021

(65) Prior Publication Data
US 2022/0284427 A1 Sep. 8, 2022

(30) Foreign Application Priority Data
Aug. 1, 2019 (JP) .................................. 2019-142552

(51) Int. Cl.
*G06Q 20/40* (2012.01)
*G06Q 30/015* (2023.01)
(Continued)

(52) U.S. Cl.
CPC ......... *G06Q 20/401* (2013.01); *G06Q 30/015* (2023.01); *G10L 25/51* (2013.01); *G16H 50/20* (2018.01)

(58) Field of Classification Search
CPC .............................. G06Q 30/015; G10L 25/51
See application file for complete search history.

(56) References Cited

U.S. PATENT DOCUMENTS 9,335,904 B2 * 5/2016 Junqua .................... G16H 40/40
10,937,526 B2 * 3/2021 Cox ..................... G06F 16/2477
(Continued)

FOREIGN PATENT DOCUMENTS

| CN | 106709728 A | 5/2017 |
| JP | 2002-157535 A | 5/2002 |

(Continued)

OTHER PUBLICATIONS

Fong KN, Chow KY, Chan BC, Lam KC, Lee JC, Li TH, Yan EW, Wong AT. Usability of a virtual reality enviro simulating an automated teller machine for assessing and training persons with acquired brain injury. J Neuroeng Rehabil. Apr. 30, 2010;7:19. doi: 10.1186/1743-0003-7-19. PMID: 20429955; PMCID: PMC28 (Year: 2010).*

(Continued)

*Primary Examiner* — Sun M Li
(74) *Attorney, Agent, or Firm* — Rimon P.C.

(57) ABSTRACT

An evaluation system includes an information acquiring unit, an evaluating unit, and a determining unit. The information acquiring unit is configured to acquire pay information relating to a consideration which a target person should pay for reception of service. The evaluating unit is configured to evaluate a cognitive function of the target person. The determining unit is configured to determine, by using acquiring of the pay information as a trigger, whether or not an evaluation for the cognitive function of the target person by the evaluating unit is required.

2 Claims, 6 Drawing Sheets

(51) Int. Cl.
*G10L 25/51* (2013.01)
*G16H 50/20* (2018.01)

(56) References Cited

U.S. PATENT DOCUMENTS

| | | | | |
|---|---|---|---|---|
| 2014/0107494 | A1* | 4/2014 | Kato | A61B 5/4088 |
| | | | | 600/300 |
| 2016/0314784 | A1* | 10/2016 | Kleppe | G10L 15/19 |
| 2018/0330178 | A1* | 11/2018 | el Kaliouby | G16H 50/20 |
| 2020/0261014 | A1* | 8/2020 | Sumi | A61B 5/4088 |
| 2021/0177340 | A1* | 6/2021 | Sumi | A61B 5/7275 |
| 2021/0183487 | A1* | 6/2021 | Teodoro | G16H 15/00 |

FOREIGN PATENT DOCUMENTS

| | | | |
|---|---|---|---|
| JP | 2009-157592 A | 7/2009 | |
| JP | 2017-59040 A | 3/2017 | |
| JP | 2017-104289 A | 6/2017 | |
| JP | 2017-176799 A | 10/2017 | |
| JP | 6337362 B2 | 6/2018 | |
| JP | 2018-190319 A | 11/2018 | |
| JP | 2019-33907 A | 3/2019 | |
| WO | WO-2015091223 A1 * | 6/2015 | A61B 5/167 |
| WO | WO-2020013302 A1 * | 1/2020 | A61B 5/0022 |

OTHER PUBLICATIONS

G. Shochat et al., "Motion-based virtual reality cognitive training targeting executive functions in acquired brain injury community-dwelling individuals: A feasibility and initial efficacy pilot," 2017 Intl Conference on Virtual Rehab (ICVR), Montreal, QC, Canada, 2017, pp. 1-8, doi:10.1109/CVR.2017 (Year: 2017).*

Glosser, Guila, et al. "Cognitive mechanisms for processing nonwords: Evidence from Alzheimer's disease." Brain and language 63.1 (1998): 32-49. (Year: 1998) (Year: 1998).*

A. Generosi, S. Ceccacci and M. Mengoni, "A deep learning-based system to track and analyze customer behavior in retail store," 2018 IEEE 8th International Conference on Consumer Electronics—Berlin (ICCE-Berlin), Berlin, Germany, 2018, pp. 1-6, doi: 10.1109/ICCE-Berlin.2018.8576169. (Year: 2018).*

J. Hakura, R. Domon and H. Fujita, "Emotion recognition method using facial expressions and situation," 2013 IEEE 12th International Conference on Intelligent Software Methodologies, Tools and Techniques (SoMeT), Budapest, Hungary, 2013, pp. 257-263, doi: 10.1109/SoMeT.2013.6645671. (Year: 2013).*

International Search Report issued in corresponding International Patent Application PCT/JP2020/027232, dated Oct. 13, 2020, with English translation.

Chinese Office Action dated Sep. 19, 2024 issued in the corresponding Chinese Patent Application No. 202080054420.0, with English machine translation.

* cited by examiner

EVALUATION SYSTEM, EVALUATION METHOD, PROGRAM, SERVER DEVICE, AND TERMINAL DEVICE

CROSS REFERENCE TO RELATED APPLICATIONS

This patent application is the U.S. National Phase under 35 U.S.C. § 371 of International Application No. PCT/JP2020/027232, filed on Jul. 13, 2020, which claims the benefit of Japanese Patent Application No. 2019-142552, dated Aug. 1, 2019, the entire contents of each are hereby incorporated by reference in their entirety.

TECHNICAL FIELD

The present disclosure generally relates to evaluation systems, evaluation methods, programs, server devices and terminal devices, and more particularly relates to an evaluation system configured to evaluate a cognitive function of a target person, an evaluation method, a program, a server device, and a terminal device.

BACKGROUND ART

Patent Literature 1 discloses an elderly person watching system for notifying a target person's guardian of a merchandise purchase state of the target person to be watched purchasing merchandise at a store. According to the system, the guardian can know about Whether or not the target person purchases unnecessary merchandise.

The system includes a management device to manage the state of the target person to be watched and a guardian terminal device carried by the guardian.

The management device includes a communications unit and a controller. The communications unit communicates with the guardian terminal device and a person detection device of detecting a person purchasing merchandise at the store. When the communications unit receives the detection information from the person detection device, the controller determines, based on the detection information received, whether or not a person purchasing merchandise at the store corresponds to the target person previously registered. When determining that the person corresponds to the target person previously registered, the controller allows the communications unit to transmit the purchase notification relating to the merchandise purchase state of the target person to the guardian terminal device.

The system disclosed in Patent Literature 1 transmits, when the target person purchases merchandise, the purchase notification to the guardian regardless of the degree of the cognitive function of the target person. It may lead to an increase in the burden on the guardian who always receives the purchase notification. Therefore, there is room for improvement in convenience of the system disclosed in Patent Literature 1.

CITATION LIST

Patent Literature

Patent Literature 1: JP 2018-190319 A

SUMMARY OF INVENTION

It is therefore an object of the present disclosure to provide an evaluation system, an evaluation method, a program, a server device, and a terminal device, which can realize improving convenience.

An evaluation system according to an aspect of the present disclosure includes an information acquiring unit, an evaluating unit, and a determining unit. The information acquiring unit is configured to acquire pay information relating to a consideration which a target person should pay for reception of service. The evaluating unit is configured to evaluate a cognitive function of the target person. The determining unit is configured to determine, by using acquiring of the pay information as a trigger, whether or not an evaluation for the cognitive function of the target person by the evaluating unit is required.

An evaluation method according to an aspect of the present disclosure includes an information acquiring processing, an evaluating processing, and a determining processing. The information acquiring processing includes acquiring pay information relating to a consideration which a target person should pay for reception of service. The evaluating processing includes evaluating a cognitive function of the target person. The determining processing includes determining, by using acquiring of the pay information as a trigger, whether or not an evaluation for the cognitive function of the target person is required.

A program according to an aspect of the present disclosure is designed to cause one or more processors to execute the evaluation method described above.

A server device according to an aspect of the present disclosure includes an information acquiring unit, an evaluating unit, and a determining unit. The information acquiring unit is configured to acquire pay information relating to a consideration which a target person should pay for reception of service. The evaluating unit is configured to evaluate a cognitive function of the target person. The determining unit is configured to determine, by using acquiring of the pay information as a trigger, whether or not an evaluation for the cognitive function of the target person by the evaluating unit is required.

A terminal device according to an aspect of the present disclosure includes an information acquiring unit, an evaluating unit, and a determining unit. The information acquiring unit is configured to acquire pay information relating to a consideration which a target person should pay for reception of service. The evaluating unit is configured to evaluate a cognitive function of the target person. The determining unit is configured to determine, by using acquiring of the pay information as a trigger, whether or not an evaluation for the cognitive function of the target person by the evaluating unit is required.

DESCRIPTION OF EMBODIMENTS

(1) Overview

In recent years, people's interest focuses on an increase in the number of patients with dementia, depending on the advent of an aging society. The dementia has a progressive symptom. Accordingly, people's interest also focuses on a mild cognitive impairment (MCI) that is a preceding stage for the dementia, from the viewpoint of the prevention of the dementia.

The MCI is a state between a normal state (healthy state) and the dementia. The MCI is mainly different from the dementia in a point whether or not patients can live independently in everyday life. More specifically, the patients with dementia have a disability in daily activities such as eating, bathing and toileting, namely basic activities of daily living (basic ADL). On the other hand, the MCI patients have no big disability in the basic ADL. However, not only the patients with dementia but also the MCI patients have a disability in the Instrumental ADL, such as shopping, housework, and money management, which are more complex activities than the basic ADL.

The symptom of MCI a deterioration degree of the cognitive function) varies widely. For example, there are also MCI patients with the degree of the cognitive function (the ability to judge something) varying from day to day. Such the MCI patients may happen to make unnecessary purchases on days when the cognitive function is deteriorated, for example.

In view of the above problems, an evaluation system 100 according to this embodiment adopts a configuration of executing an evaluation for the cognitive function of the purchaser when the purchaser makes an unnatural purchase. Then if finding the cognitive function of the purchaser being deteriorated when the unnatural purchase is made, the evaluation system 100 adopts a configuration of notifying a person of it.

Figure 1:
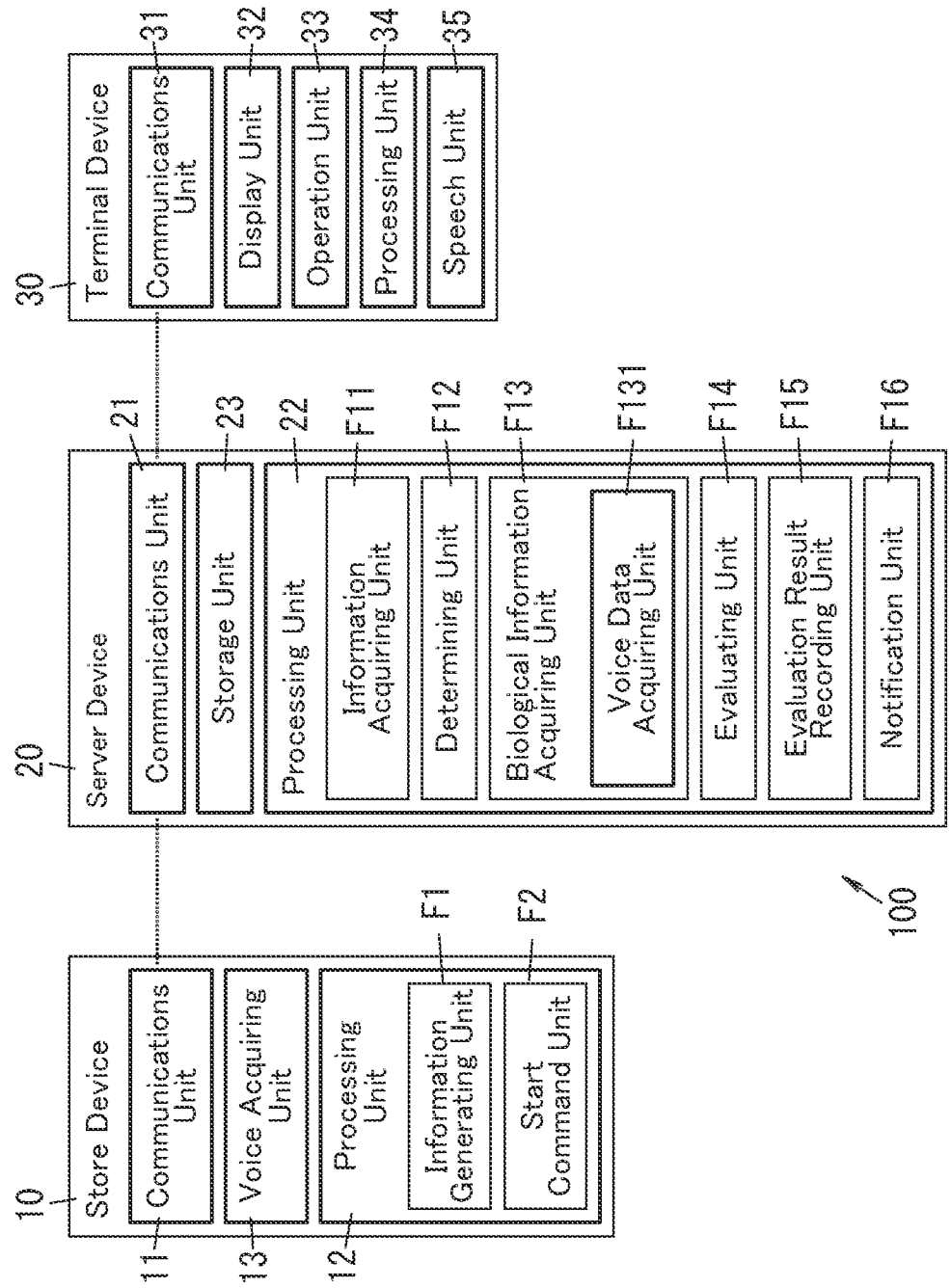
FIG. 1 is a block diagram of an evaluation system according to an exemplary embodiment.
Figure 3:
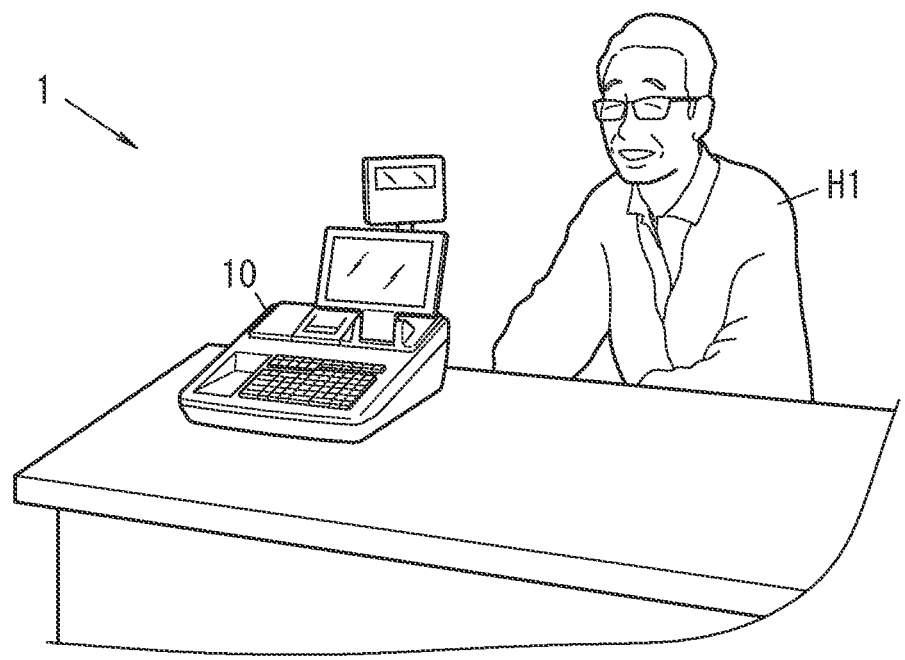
FIG. 3 is a schematic drawing of an exemplary store where a store device applied to the evaluation system is installed.

More specifically, the evaluation system 100 according to this embodiment includes an information acquiring unit F11, an evaluating unit F14, and a determining unit F12, as illustrated in FIG. 1. The information acquiring unit F11 is configured to acquire pay information relating to a consideration which a target person H1 (purchaser) (see FIG. 3) should pay for reception of service. The evaluating unit F14 is configured to evaluate a cognitive function of the target person H1. The determining unit F12 is configured to determine, by using acquiring of the pay information as a trigger, whether or not an evaluation for the cognitive function of the target person H1 by the evaluating unit F14 is required. When determining that the evaluation for the cognitive function of the target person H1 should be required, the determining unit F12 allows the evaluating unit F14 to evaluate the cognitive function of the target person H1.

The evaluation system 100 according to this embodiment further includes a notification unit F16, as illustrated in FIG. 1. The evaluating unit F14 is configured to express the cognitive function of the target person H1 by a numerical value that represents a deterioration degree of the cognitive function of the target person H1. The notification unit F16 is configured to notify at least one, selected from the target person H1 oneself, a family of the target person H1 and a guardian of the target person H1, of cancel information for cancelling paying of the consideration, when the numerical value representing the deterioration degree of the cognitive function evaluated by the evaluating unit F14 is greater than a prescribed threshold.

The evaluation system 100 according to this embodiment can decide whether or not the purchase judgement is caused by a deterioration in the cognitive function of the purchaser, when the unnatural purchase is made. Therefore, a person can take subsequent, assuming that the cognitive function is deteriorated upon shopping, for example. Consequently, the evaluation system 100 can realize improving convenience.

Furthermore, the evaluation system 100 according to this embodiment determines, by using acquiring of the pay information as a trigger, the cognitive function of the target person H1 as needed, and further allows the notification unit F16 to execute the notification as needed. Therefore, the evaluation system 100 can reduce a frequency by which the notification is executed, for example. Consequently, the evaluation system 100 can realize improving convenience.

Also regarding the target person H1 who oneself is not aware of the MCI or the dementia, the evaluation system 100 according to this embodiment can determine, by using acquiring of the pay information as a trigger, whether or not an evaluation for the cognitive function by the evaluating unit F14 is required. Therefore, the evaluation system 100 can contribute to early discovery of patients with the MCI or the dementia.

(2) Details

Hereinafter, an evaluation system 100 according to this embodiment will be described in more detail with reference to FIGS. 1 to 4.

(2.1) Overall Configuration

Figure 2:
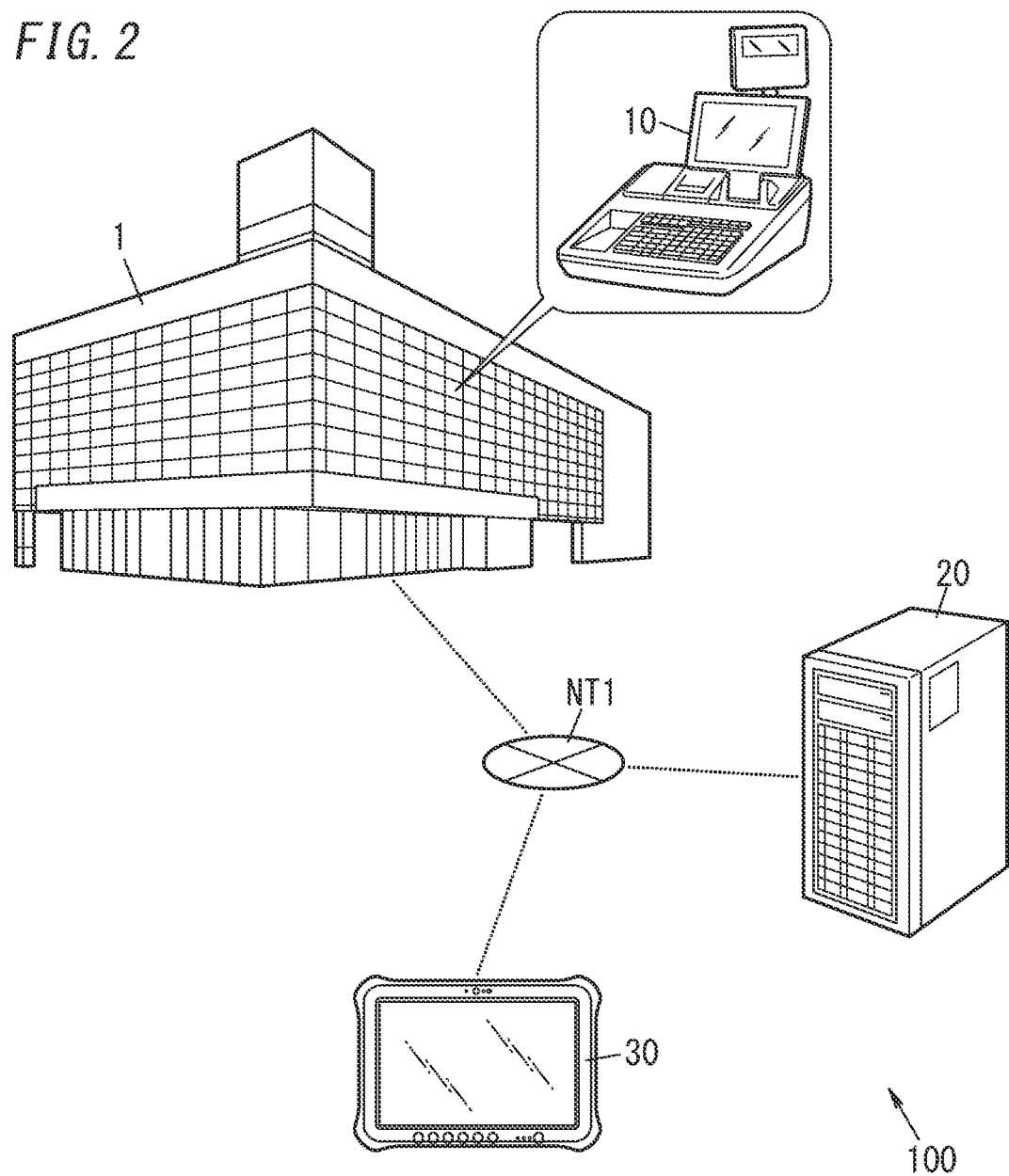
FIG. 2 is a schematic drawing schematically illustrating the evaluation system.

FIGS. 1 and 2 show the configuration of the evaluation system 100 according to this embodiment.

As illustrated in FIG. 1, the evaluation system 100 includes a store device 10, a server device 20 and a terminal device 30. Note that, the store device 10 and the terminal device 30 are not essential components for the evaluation system 100, and may be omitted from the components of the evaluation system 100.

As illustrated in FIG. 2, the store device 10 is installed at a store 1. The server device 20 constitutes a main part of the evaluation system 100 according to this embodiment. The server device 20 is installed at a facility of an organization providing service by the evaluation system 100 according to this embodiment, for example. The terminal device 30 is, for example, an information terminal carried by a target person H1, a family of the target person H1 or a guardian of the target person H1 (hereinafter, they may be sometimes referred to as a "user").

As described above, the store device 10 is installed at the store 1. The store 1 in this embodiment means an object, which provides service to customers, and to which the customers pay a consideration for the service provided.

In this embodiment, the service provision includes, for example, selling merchandise (articles; tangible objects).

Examples of the store 1 may include a retail store directly selling merchandise with respect to customers. Examples of the retail store may include a convenience store, a supermarket, a department store, a drug store, a clothing store, an electronics retail store and a hardware store.

Furthermore, examples of the store 1 may include a virtual store indirectly selling merchandise with respect to customers. The virtual store is configured to receive orders for merchandise from customers via a telecommunications line NT1 such as the Internet or telephone line, send the merchandise to the customers in accordance with the orders, and receive the consideration (the price) from the customers by electronic payment, cash registration, cash on delivery or the like. Examples of the virtual store may include a mail-order business. Examples of a form of the mail-order business may include online shopping, infomercials, and sales by catalog.

In this embodiment, the service provision may include providing intangible objects. Examples of providing the intangible objects may include providing service as giving utility, satisfaction, or the like to customers. Examples of the store 1 (may include the virtual store) providing the intangible objects may include a restaurant, an entertainment facility, a travel agency, a medical facility, an insurance agency, and a video viewing service (may include online).

In this embodiment, a form of the consideration to be paid for the service provision is not particularly limited. Examples of a payment method of the consideration include payment processing by a credit card, a prepaid card, electronic money, a reward card (points card), crypto assets (so-called electronic money) and cash.

Hereinafter, for convenience of explanation, the store device 10 is assumed to be installed at a retail store (e.g., an electronics retail store) as the store 1.

In the store 1, a plurality of kinds of merchandise are sold with being displayed in the store, for example. Customers select a desired kind of merchandise from the plurality of kinds of merchandise displayed in the store, and can purchase the merchandise by making payment for the merchandise. The "payment" for merchandise means, when an ownership of the merchandise is transferred from a seller (store 1) to a buyer (customer), a settlement processing on the buyer side to be required for the buyer to pay the seller the consideration (price) for the transfer (i.e., a settlement processing to be required for buying and selling).

The store device 10 in this embodiment is a point of sales (POS) terminal. In particular, the store device 10 in this embodiment is a so-called "ID-POS" capable of dealing with ID-POS data. The "ID-POS data" mentioned herein is data where a "customer ID" as an identification information (ID) of a customer is added to the POS data. This type of POS terminal (ID-POS) acquires the identification information of the customer (customer ID) by authenticating the customer when the customer make a purchase. Authenticating of the customer may be realized by various cards such as a membership card, a reward card (points card) and a credit card. Alternatively, authenticating of the customer may be realized by communication with a mobile information terminal carried by the customer, or biometric authentication (may include face authentication).

The store device 10 as above is capable of transmitting the pay information (as data) for purchasing the merchandise at the store 1 to the server device 20 via the network NT1, for example. In particular, the store device 10 in this embodiment is capable of dealing with the ID-POS data. Therefore, the store device 10 can output the information about the merchandise to be purchased (i.e., the pay information) with being associated with the identification information of the customer (customer ID) before the accounting is done or while the accounting is done.

More specifically, the store device 10 includes a communications unit 11 and a processing unit 12, as illustrated in FIG. 1. The store device 10 in this embodiment further includes a voice acquiring unit 13.

The communications unit 11 is a communication interface. The communications unit 11 is a communication interface connectable with the telecommunications line NT1, and has a function of communicating with the other device via the telecommunications line NT1 (see FIG. 2). Accordingly, the store device 10 is configured to communicate with the server device 20 via the telecommunications line NT1. The telecommunications line NT1 is constituted by a network compliant with a single communication protocol, for example. Alternatively, the telecommunications line NT1 may be constituted by two or more networks compliant with different communication protocols. The communication protocol may be selected from well-known various wired communication standards and wireless communication standards. The telecommunications line NT1 may include data communication devices such as a repeater hub, a switching hub, a bridge, a gateway, and a router, although simplified in FIG. 2.

The voice acquiring unit 13 includes a microphone. The microphone converts a sound including a voice emitted by the customer into a voice data (voice signal), and externally outputs the voice data via the communications unit 11. In this embodiment, the voice acquiring unit 13 allows the communications unit 11 to transmit the voice data to the server device 20 via the telecommunications line NT1.

The processing unit 12 is configured to perform the overall control of the store device 10, namely control operations of the communications unit 11 and the voice acquiring unit 13. The processing unit 12 may include a computer system including one or more processors (microprocessors) and one or more memories, for example. The computer system performs the function of the processing unit 12 by making the one or more processors execute one or more programs (applications) stored in the one or more memories. In this embodiment, the one or more programs to be executed by the one or more processors are stored in advance in the one or more memories of the processing unit 12. However, this is only an example and should not be construed as limiting. The one or more programs may also be distributed after having been stored in a non-transitory storage medium such as a memory card or downloaded via a telecommunications line such as the Internet.

As illustrated in FIG. 1, the processing unit 12 includes an information generating unit F1 and a start command unit F2. The information generating unit F1 and the start command unit F2 represent functions to be realized by the processing unit 12 rather than substantial components.

The information generating unit F1 generates the pay information relating to the consideration which the customer (target person H1) should pay for reception of the service. In this embodiment, since the store 1 is a retail store, the reception of the service includes acquisition of merchandise (purchase of articles). The pay information generated by the information generating unit F1 may include: information about the price of an individual piece of merchandise related to the purchase (i.e., the unit price); information about the total price of merchandise related to the purchase; information about the number of pieces of merchandise related to the purchase (i.e., the quantity); and information about a category of merchandise related to the purchase.

The information about the price of merchandise may include at least one selected from a sticker price, a list price, and a suggested retail price.

The information about the number of pieces of merchandise may include: information about the number of pieces of merchandise by kind related to the purchase; and information about the total number of all pieces of merchandise related to the purchase.

The category of merchandise is a label for classifying the merchandise by its use, its function, a customer base, or the like. The information about the category of merchandise may include information about a large category, a medium category and a small category to which the merchandise belongs. The large category may correspond to a relatively large classification category such as foods, clothes, pharmaceuticals, beauty-related products, electrical appliances, or daily necessities. The medium category may correspond to a classification category where the large category is further classified into two or more groups. When the large category is the electrical appliances, examples of the medium category may include vacuum cleaners, washing machines, refrigerators, video devices, lighting devices, information terminals and air conditioners. The small category may correspond to a classification category where the medium category is further classified into two or more groups. When the medium category is the washing machines, examples of the small category may include washing capacities of the washing machines and manufactures of the washing machines.

In this embodiment, the information generating unit F1 generates the pay information before the accounting is completed (i.e., before the settlement processing is completed). That is to say, the information generating unit F1 generates the pay information at any time point while the store device 10 (see FIG. 3) as the POS terminal optically reads merchandise information about one or more pieces of merchandise sequentially, or more preferably at a time point when the store device 10 has read merchandise information about the last piece of merchandise. The information generating unit F1 transmits the pay information generated to the server device 20 via the communications unit 11. In this embodiment, the information generating unit F1 associates the pay information with the identification information (customer ID) of the customer (target person H1) and then transmits it to the server device 20.

The start command unit F2 outputs a command to start acquisition of the information (biological information) of the customer (target person H1) to be used by the evaluating unit F14 for executing the evaluation for the cognitive function. More specifically, the start command unit F2 allows the microphone of the voice acquiring unit 13 to start operation to convert the sound including the voice emitted by the customer (target person H1) into the voice data, in accordance with an acquisition command (described later) received from the server device 20. The voice acquiring unit 13 then allows the communications unit 11 to transmit the voice data to the server device 20.

As one example, the voice data may be data of any voice autonomously emitted by the target person H1, after the store device 10 receives the acquisition command and then the sound collecting operation of the microphone is started. The voice of the target person H1 collected by the microphone may include the contents relate to the payment, or may have no relation to the payment. Alternatively, the voice data may be data of a voice emitted by the target person H1 reading aloud a prescribed fixed phrase.

As illustrated in FIG. 1, the server device 20 includes a communications unit 21, a processing unit 22 and a storage unit 23.

The communications unit 21 is a communication interface. The communications unit 21 is a communication interface connectable with the telecommunications line NT1, and has a function of communicating with the other device via the telecommunications line NT1 (see FIG. 2). Accordingly, the server device 20 is configured to communicate with the store device 10 via the telecommunications line NT1. Furthermore, the server device 20 is configured to communicate with the terminal device 30 via the telecommunications line NT1. The communications unit 21 may communicate with the store device 10 and the terminal device 30 using the same communication protocol, or using different communication protocols respectively. The storage unit 23 is a device for storing therein information. The storage unit 23 may include a Read Only Memory (ROM), a Random Access Memory (RAM), an EEPROM, or the like.

The processing unit 22 may include a computer system including one or more processors (microprocessors) and one or more memories, for example. The computer system performs the function of the processing unit 22 by making the one or more processors execute one or more programs (applications) stored in the one or more memories.

The processing unit 22 is configured to perform the overall control of the server device 20, namely control operations of the communications unit 21 and the storage unit 23. Also as illustrated in FIG. 1, the processing unit 22 includes an information acquiring unit F11, a determining unit F12, a biological information acquiring unit F13, an evaluating unit F14, an evaluation result recording unit F15 and a notification unit F16. Note that, the information acquiring unit F11, the determining unit F12, the biological information acquiring unit F13, the evaluating unit F14, the evaluation result recording unit F15, and the notification unit F16 represent functions to be realized by the processing unit 22 rather than substantial components. In short, the server device 20 includes the information acquiring unit F11, the evaluating unit F14 and the determining unit F12.

The information acquiring unit F11 acquires the pay information generated by the information generating unit F1 of the store device 10 via the communications unit 21. The information acquiring unit Fit associates the acquired pay information with the identification information (customer ID) of the customer and allows the storage unit 23 to record it. That is to say, the evaluation system 100 according to this embodiment includes the information acquiring unit F11 configured to acquire the pay information relating to the consideration which the target person H1 (customer) should pay for reception of service.

The determining unit F12 determines, by using acquiring of the pay information as a trigger, whether or not the evaluation for the cognitive function of the target person H1 (customer) is required. In this embodiment, the determining unit F12 determines, by processing the pay information of the target person H1 recorded in the storage unit 23, whether or not the evaluation for the cognitive function of the target person H1 is required. That is to say, the determining unit F12 determines, based on the contents of the pay information acquired, whether or not the evaluation for the cognitive function is required.

In this embodiment, the pay information (to be used by the determining unit F12 for determining whether or not the evaluation for the cognitive function is required) includes information about an amount of money as the consideration.

The determining unit F12 determines that the evaluation for the cognitive function should be required, when finding that the amount of money is greater than or equal to a prescribed threshold, for example. The amount of money may be the price of one piece of merchandise (unit price), or the total price of the two or more pieces of merchandise. The threshold may be set as appropriate by the target person H1 oneself, a family of the target person H1, or a guardian of the target person H1 using the terminal device 30.

In this embodiment, the pay information (to be used by the determining unit F12 for determining whether or not the evaluation for the cognitive function is required) further includes information about a combination in the two or more pieces of merchandise acquired. Also, the pay information further includes information about the number of pieces of merchandise acquired.

That is to say, for example, when a person purchases the two or more pieces of merchandise, the determining unit F12 determines, based on the combination in the two or more pieces of merchandise to be purchased, whether or not the evaluation for the cognitive function is required. The "combination in the two or more pieces of merchandise to be purchased" mentioned herein may include the number of the two or more pieces of merchandise to be purchased.

For example, the determining unit F12 determines that the evaluation for the cognitive function should be required, when finding that the combination in the two or more pieces of merchandise to be purchased is absurd (unreasonable). For example, the determining unit F12 decides that the combination in the merchandise to be purchased should be absurd, when finding that two or more non-expendable supplies belonging to the same medium category (or the same small category) are purchased at one time (or within a short period), more specifically, when finding that ten refrigerators are purchased simultaneously, or when finding that a liquid crystal television, an organic electroluminescence (EL) television, a plasma television and a rear projection television with the same size are purchased simultaneously. Also, the determining unit F12 decides that the combination in the merchandise to be purchased should be absurd, when finding that a relationship between the two or more pieces of merchandise to be assumed to be used simultaneously is absurd, more specifically, when finding that clothes with different sizes (e.g., tops with a small size and bottoms with an extra-large size) are purchased simultaneously. Information about a reference combination in merchandise which may be absurd (unreasonable) is previously recorded in the storage unit 23.

The pay information (to be used by the determining unit F12 for determining whether or not the evaluation for the cognitive function of the target person H1 is required) may be pay information about paying at one time. In other words, the determining unit F12 may determine, based on the pay information about paying at one time, whether or not the evaluation by the evaluating unit F14 is required.

Alternatively, the pay information (to be used by the determining unit F12 for determining whether or not the evaluation for the cognitive function of the target person H1 is required) may be a history of the pay information within a prescribed time period (e.g., one day, two days, three days, one week, two weeks, one month, two months, three months, six months, one year, or the like). In other words, the determining unit F12 may determine, based on the history of the pay information within the prescribed time period, whether or not the evaluation by the evaluating unit F14 is required.

Needless to say, the determining unit F12 may perform a determination about whether or not the evaluation by the evaluating unit F14 is required based on bath the pay information about paying at one time, and based on the history of the pay information within the prescribed time period.

The biological information acquiring unit F13 acquires the biological information of the target person H1 (customer), when the determining unit F12 determines that the evaluation for the cognitive function should be required. In this embodiment, the biological information of the target person H1 is voice data which is information about a voice emitted by the target person H1. Accordingly, the biological information acquiring unit F13 includes a voice data acquiring unit F131 for acquiring the voice data.

The voice data acquiring unit F131 allows the communications unit 21 to transmit the acquisition command to the store device 10, when the determining unit F12 determines that the evaluation for the cognitive function should be required. The voice data acquiring unit F131 acquires the voice data, which is transmitted from the store device 10 as a response to the acquisition command, via the communications unit 21. The voice data acquiring unit F131 associates the acquired voice data with the target person H1, and allows the storage unit 23 to record the voice data associated with target person H1.

In short, the evaluation system 100 according to this embodiment includes the voice data acquiring unit F131. The voice data acquiring unit F131 acquires the voice data of the target person H1, when the determining unit F12 determines that the evaluation by the evaluating unit F14 is required.

The evaluating unit F14 evaluates the cognitive function of the target person H1 (customer) based on the biological information of the target person H1, when the determining unit F12 determines that the evaluation for the cognitive function should be required. In this embodiment, the evaluating unit F14 evaluates the cognitive function of the target person H1 by processing the voice data acquired by the voice data acquiring unit F131 and recorded in the storage unit 23.

In this embodiment, the evaluating unit F14 evaluates the cognitive function of the target person H1, using a feature (feature quantity) extracted from the voice data.

The feature quantity to be used for the evaluation for the cognitive function of the target person H1 may include the quantity relating to a first formant frequency or a second formant frequency of a vowel sound, which is in a syllable included in the voice of the target person H1, denoted by the voice data. The first formant frequency is a frequency corresponding to the lowest frequency peak of a plurality of frequency peaks included in a voice emitted by a human. The second formant frequency is a frequency corresponding to the second lowest frequency peak of the plurality of frequency peaks included in the voice emitted by the human.

The feature quantity to be used for the evaluation for the cognitive function of the target person H1 may include a difference between a sound pressure of a consonant sound and a sound pressure of a vowel sound succeeding to the consonant sound, which are in an open syllable included in the voice of the target person H1, denoted by the voice data.

The feature quantity to be used for the evaluation for the cognitive function of the target person H1 may include variation in differences, each of which is between a sound pressure of each of consonant sounds and a sound pressure of a vowel sound succeeding to a corresponding consonant sound, of vowel sounds, which are in a plurality of open syllables included in the voice of the target person H1, denoted by the voice data.

Note that, see, for example, JP 6337362 B1, regarding details about the feature quantity of the voice of the target person H1 to be used by the evaluating unit F14 for the evaluation for the cognitive function of the target person H1.

The evaluating unit F14 outputs an evaluation result relating to the cognitive function of the target person H1. The evaluation result is expressed by a numerical value that represents a deterioration degree of the cognitive function of the target person H1, for example. The evaluating unit F14 may express the acquired evaluation result of the cognitive function, for example, by a numerical value denoting a corresponding stage of two or more predetermined stages (e.g., a second stage of five stages).

The evaluation result recording unit F15 associates, with the pay information, the evaluation result of the cognitive function of the target person H1, acquired by the evaluating unit F14, and records it in the storage unit 23. In other words, the evaluation system 100 according to this embodiment includes the evaluation result recording unit F15 configured to associate, with the pay information, the evaluation result relating to the cognitive function of the target person obtained by the evaluating unit F14, and record the evaluation result associated with the pay information.

The notification unit F16 notifies the store device 10 and the terminal device 30 of result information about the evaluation result by the evaluating unit F14. For example, when finding the numerical value representing the deterioration degree of the cognitive function evaluated by the evaluating unit F14 is greater than a prescribed threshold (hereinafter, sometimes referred to as "when finding that the target person H1 has dementia at a high possibility"), the notification unit F16 notifies the store device 10 and the terminal device 30 of the result information. The notification unit F16 may notify the store device 10 and the terminal device 30 of the result information without depending on the contents of the evaluation result.

The result information (of which the notification unit F16 notifies the store device 10 and the terminal device 30) may be the evaluation result itself (e.g., a numerical value), acquired by the evaluating unit F14, or a form different from the numerical value.

In this embodiment, the notification unit F16 notifies, when finding that the target person H1 has dementia at a high possibility, the store device 10 of sales caution information. The sales caution information includes, for example, information showing that the target person H1 has dementia at a high possibility. The sales caution information may include information for instructing that the settlement processing for merchandise be cancelled.

As above, transmitting the sales caution information to the store device 10 can prompt a salesperson operating the store device 10 in the store 1 to stop selling merchandise (i.e., stop the settlement processing). Therefore, the evaluation system 100 can prevent the target person H1 from purchasing unnecessary merchandise.

Also, the notification unit F16 further notifies, when finding that the target person H1 has dementia at a high possibility, the terminal device 30 of cancel information. The cancel information may include, for example, one or more pieces of information selected from: the pay information; information about a time limit by which return of the merchandise is permitted; and information about procedures required for return of the merchandise.

For example in Japan, there is a system (a so-called "cooling off system") in which the buyer can unconditionally retract the purchase order or cancel the contracts based on the law without explanation only for certain contracts in a certain period of time. The information about the procedures required for return of the merchandise may include information about the cooling off system. Examples of the law relating to the cooling off system include the Act on Specified Commercial Transactions. Also, the information about the procedures required for return of the merchandise may include information for cancelling application for contract or the manifestation of intention to accept the contract based on the Consumer Contract Act. Alternatively, if the seller independently sets the time limit by which return of the merchandise is permitted, the information about the procedures required for return of the merchandise may include information about the time limit.

As above, notifying the terminal device 30 of the cancel information can increase chances that the user of the terminal device 30 can cancel the settlement processing (payment), even after the settlement processing is completed in spite of transmission of the sales caution information to the store device 10. That is to say, unnecessary merchandise purchased by the target person H1 can be cancelled.

The server device 20 may notify the terminal device 30 of the cancel information, after receiving from the store device 10 a notification that the settlement processing is completed (i.e., after the settlement processing is completed and the payment is also completed at the store 1).

In short, the evaluation system 100 according to this embodiment includes the notification unit F16. The notification unit F16 is configured to notify at least one, selected from the target person H1 oneself, a family of the target person H1 and a guardian of the target person H1, of the cancel information for cancelling the payment, when the numerical value representing the deterioration degree of the cognitive function evaluated by the evaluating unit F14 is greater than the prescribed threshold.

In the above example, the notification unit F16 notifies both the store device 10 and the terminal device 30 of the result information. However, it is only an example and should not be construed as limiting. The notification unit F16 may notify only either the store device 10 or the terminal device 30 of the result information. Note that, the notification unit F16 preferably notifies at least the terminal device 30 of the result information.

As described above, the terminal device 30 is an information terminal. As one example, the terminal device 30 may be implemented as a mobile terminal, a mobile phone or a personal computer. The mobile terminal may be a smartphone or a tablet terminal, for example. The terminal device 30 presents the cancel information received from the server device 20. In this embodiment, the terminal device 30 is assumed to be a tablet terminal (see FIG. 2).

As illustrated in FIG. 1, the terminal device 30 includes a communications unit 31, a display unit 32, an operation unit 33 and a processing unit 34. The terminal device 30 in this embodiment further includes a speech unit 35.

The communications unit 31 is a communication interface. The communications unit 31 is a communication interface connectable with the telecommunications line NT1, and has a function of communicating with the other device via the telecommunications line NT1. Accordingly, the terminal device 30 is configured to communicate with the server device 20 via the telecommunications line NT1.

The display unit 32 displays information based on data and so on received at the communications unit 31. The display unit 32 includes a Liquid Crystal Display (LCD) or an organic EL display, for example. The display unit 32 displays, for example, the result information (cancel information) received from the server device 20.

The operation unit 33 accepts an operation input from the user and then outputs a signal in accordance with the operation input accepted. In this embodiment, since the terminal device 30 is assumed to be a generic tablet terminal, the display unit 32 and the operation unit 33 are formed integrally with each other as a touch panel display. The terminal device 30 as the touch panel display decides, when the operation unit 33 detects an operation (e.g., a tapping operation, a swipe operation, or a drag operation) to an object such as a button on each screen displayed by the display unit 32, that the object (such as the button) has been operated. That is to say, the display unit 32 and the operation unit 33 function as a user interface of accepting the operation input from the user in addition to displaying various information.

The speech unit 35 includes a loudspeaker and a microphone. The microphone converts a sound including a voice emitted by the user into voice data (voice signal), and then externally outputs the voice data via the communications unit 31. The loudspeaker converts voice data (voice signal) externally received via the communications unit 31 into a voice (sound), and then outputs the voice.

The processing unit 34 is configured to perform the overall control of the terminal device 30, namely control operations of the communications unit 31, the display unit 32, the operation unit 33 and the speech unit 35. The processing unit 34 may include a computer system including one or more processors (microprocessors) and one or more memories, for example. The computer system performs the function of the processing unit 34 by making the one or more processors execute one or more programs (applications) stored in the one or more memories. In this embodiment, the one or more programs to be executed by the one or more processors are stored in advance in the one or more memories of the processing unit 34. However, this is only an example and should not be construed as limiting. The one or more programs may also be distributed after having been stored in a non-transitory storage medium such as a memory card or downloaded via a telecommunications line such as the Internet.

(2.2) Operation

Figure 4:
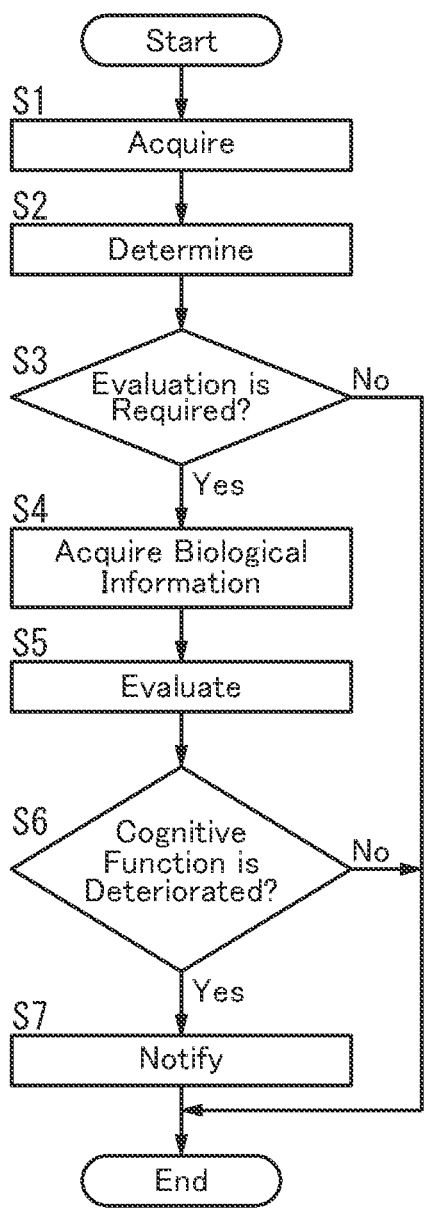
FIG. 4 is a flowchart showing one example of an evaluation method according to an exemplary embodiment.

Next, an exemplary operation about how the evaluation system 100 according to this embodiment operates will be briefly described with reference to FIG. 4.

The customer picks up one or more pieces of merchandise displayed in the store 1 as appropriate, and requests the salesperson to execute the settlement processing at a payment place (see FIG. 3) in the store 1. The salesperson allows the store device 10 to read the merchandise information in accordance with the request. The store device 10 generates the pay information based on the merchandise information read. The store device 10 transmits the pay information generated to the server device 20, and the server device 20 accordingly acquires the pay information (in an information acquiring processing S1). When acquiring the pay information, the server device 20 determines, based on the pay information acquired, whether or not the evaluation for the cognitive function is required (in a determining processing S2).

In determining about whether or not the evaluation for the cognitive function is required (in a step S3), the server device 20 transmits the determination result to the store device 10 and/or the terminal device 30 as needed and finishes the operation, if determining that the evaluation is not required (if the answer is No in the step S3). On the other hand, the server device 20 allows the communications unit 21 to transmit the acquisition command to the store device 10, if determining that the evaluation is required (if the answer is Yes in the step S3). The store device 10 acquires the biological information (the voice data of the target person herein) of the target person H1 by receiving the acquisition command and recoding the voice of the target person H1 (in a biological information acquiring processing S4). The store device 10 then transmits to the server device 20 the biological information acquired.

When receiving the biological information, the server device 20 evaluates the cognitive function of the target person H1 by processing the biological information received (in an evaluating processing S5).

In evaluating of the cognitive function (in a step S6), the server device 20 transmits the evaluation result to the store device 10 and/or the terminal device 30 as needed and finishes the operation, if the result that the cognitive function of the target person H1 is high (i.e., that the target person has the dementia or the MCI at a low possibility) is obtained (if the answer is No in the step S6). On the other hand, the server device 20 notifies the store device 10 and/or the terminal device 30 of the result information (in a notification processing S7), if the result that the cognitive function of the target person H1 is deteriorated (i.e., that the target person has the dementia or the MCI at a high possibility) is obtained (if the answer is Yes in the step S6). Here, the result information of which the server device 20 notifies the terminal device 30 may include the cancel information, as described above.

When the store device 10 and/or the terminal device 30 receive the result information, the salesperson or the user of the terminal device 30 may take appropriate measures based on the result information.

As above, the evaluation system 100 according to this embodiment determines, by using acquiring of the pay information as a trigger, the cognitive function of the target person H1 as needed, and further the notification unit F16 notifies the store device 10 and/or the terminal device 30 of the result information as needed. Therefore, the evaluation system 100 can reduce a frequency by which the notification is executed. Consequently, the evaluation system 100 can realize improving convenience. In addition, when the evaluating unit F14 determines that the cognitive function of the target person H1 is deteriorated on shopping, the notification of the cancel information is executed. Therefore, the evaluation system 100 can increase the chances that a person received the notification can cancel the purchase, and consequently can realize improving convenience.

(3) Variations

Various embodiments of the present disclosure are not limited to the exemplary embodiment described above. The exemplary embodiment may be readily modified in various manners depending on a design choice or any other factor, as long as the purpose of the present disclosure can be attained. The functions similar to the evaluation system 100 according to the exemplary embodiment may also be implemented as, for example, an evaluation method, a computer program, or a non-transitory storage medium that stores the computer program.

An evaluation method according to one aspect includes an information acquiring processing, an evaluating processing, and a determining processing. The information acquiring processing includes acquiring pay information relating to a consideration which a target person H1 should pay for reception of service. The evaluating processing includes evaluating a cognitive function of the target person H1. The determining, processing includes determining, by using acquiring of the pay information as a trigger, whether or not an evaluation for the cognitive function of the target person H1 is required.

A (computer) program according to one aspect is a computer program designed to cause one or more processors to execute the evaluation method described above.

Hereinafter, variations of the exemplary embodiment described above will be listed. The variations to be described below may be adopted in combination as appropriate.

The evaluation system 100 according to the present disclosure includes a computer system, for example, in the server device 20. The computer system may include a processor and a memory as principal hardware components. The functions of the server device 20 may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be implemented as a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits include a system LSI, a very large-scale integrated circuit (VLSI), and an ultra-large scale integrated circuit (VLSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be integrated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

Also, the plurality of functions of the evaluation system 100 are integrated together in a single housing, but this is not an essential configuration for the evaluation system 100. Alternatively, the plurality of functions of the evaluation system 100 may be distributed in multiple different housings. Still alternatively, at least some functions of the evaluation system 100 (e.g., some functions of the server device 20) may be implemented as a cloud computing system as well.

Conversely, at least some functions of the evaluation system 100 distributed into a plurality of devices in the exemplary embodiment described above may be integrated together in a single housing. For example, some functions of the evaluation system 100 distributed into the server device 20 and the store device 10 may be integrated together in a single housing.

(3.1) First Variation

Figure 5:
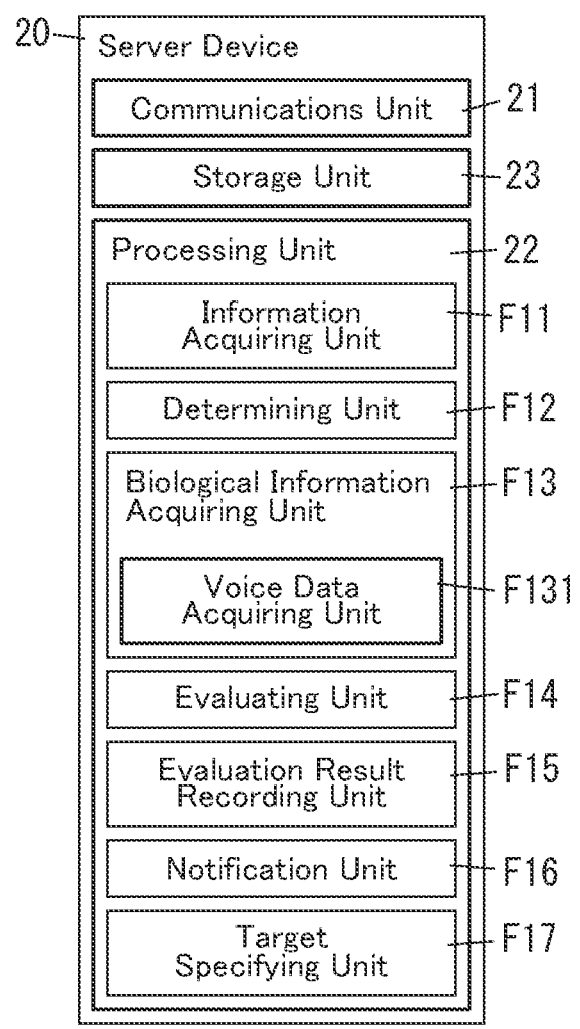
FIG. 5 is a block diagram of a server device applied to a first variation of the evaluation system.

In the exemplary embodiment described above, the determining unit F12 determines whether or not the evaluation by the evaluating unit F14 is required with respect to all customers. However, the determining unit F12 of the evaluation system 100 may determine whether or not the evaluation by the evaluating unit F14 is required with respect to only target person(s) H1 previously registered, in this case, the server device 20 may further include a target specifying unit F17, as illustrated in FIG. 5.

In this variation, for example, the storage unit 23 of the server device 20 records information (e.g., name, age and sex) relating to the target person H1 previously registered and voiceprint information as information about a voiceprint of the target person H1 previously acquired. The information (name, age and sex) and the voiceprint information are recorded to be associated with each other in the storage unit 23. The information (name, age and sex) relating to the target person H1 and the voiceprint information of the target person H1 are registered, for example, by the user (the target person H1 oneself, a family thereof, or a guardian thereof) inputting their information, using the terminal device 30, and then the terminal device 30 transmitting to the server device 20 their information inputted. That is to say, the evaluation system 100 (i.e., the processing unit 22 of the server device 20) in this variation includes a registration unit for registering the target person H1.

In this variation, for example, the store device 10 transmits, to the server device 20, the pay information together with the voice data of the customer acquired by the voice acquiring unit 13. When receiving the pay information and the voice data from the store device 10, the server device 20 allows the target specifying unit F17 to contrast the voice data and the voiceprint information recorded in the storage unit 23 to determine whether or not the customer is the target person H1 and specify the target person H1. Thus, the server device 20 can determine, only when the customer is the target person H1 previously registered, whether or not the evaluation by the evaluating unit F14 is required.

In short, the evaluation system 100 according to this variation further includes the target specifying unit F17. The target specifying unit F17 is configured to specify the target person H1 based on the voice data as information about the voice emitted by the target person H1 and the voiceprint information as information about the voiceprint of the target person H1 previously acquired.

This is only an example and should not be construed as limiting. The server device 20 may determine whether or not the customer is the target person H1 registered, based on the customer ID added to the ID-POS data.

(3.2) Second Variation

In the exemplary embodiment described above, the voice acquiring unit 13 is provided for the store device 10. However, the voice acquiring unit 13 may be provided for a device other than the store device 10 (e.g., an information terminal such as a mobile terminal, a mobile phone, or a personal computer, carried by the target person H1).

Also in this variation, the information (e.g., name, age and sex) relating to the target person H1 is previously registered in the server device 20, like the first variation. In this variation, the information relating to the target person H1 further includes identification information of the information terminal carried by the target person H1.

When the determining unit F12 determines that the evaluation by the evaluating unit F14 should be required, the biological information acquiring unit F13 of the server device 20 transmits the acquisition command to the information terminal to acquire the voice data from the information terminal. The evaluating unit F14 processes the voice data acquired to evaluate the cognitive function of the target person H1.

The information terminal in this variation may be the terminal device 30 in the exemplary embodiment described above.

(3.3) Third Variation

Figure 6:
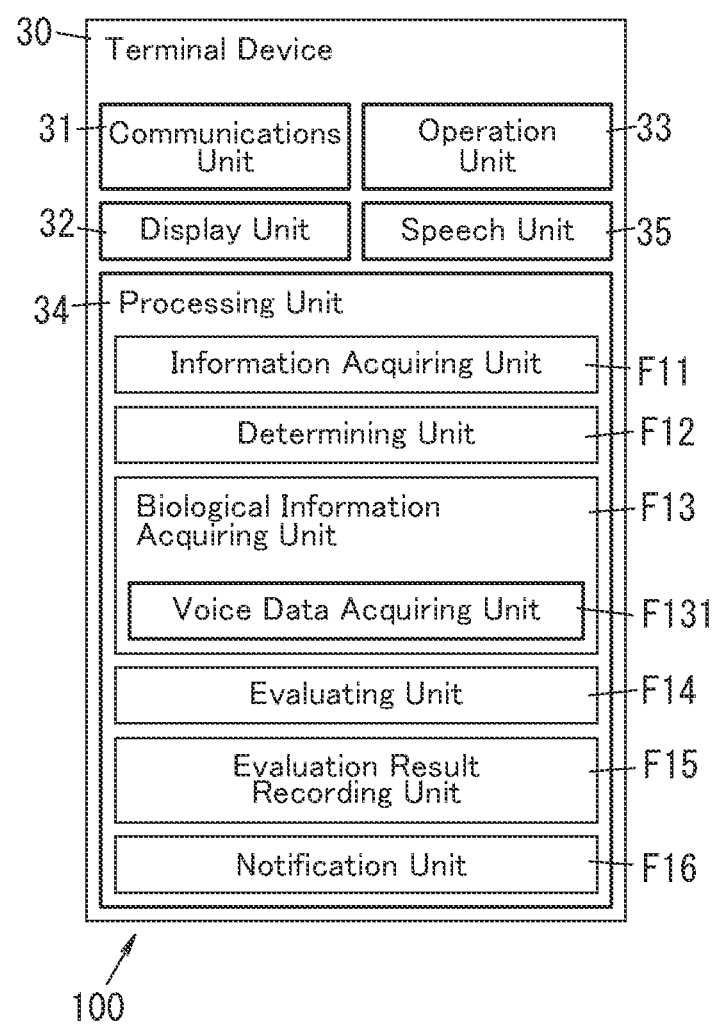
FIG. 6 is a block diagram of a terminal device applied to a third variation of the evaluation system.

In this variation, all the functions of the evaluation system 100 are integrated together in the terminal device 30, as illustrated in FIG. 6. That is to say, the processing unit 34 of the terminal device 30 in this variation has the functions of the information acquiring unit F11, the determining unit F12, the biological information acquiring unit F13, the evaluating unit F14 and the evaluation result recording unit F15. In short, in this variation, the cognitive function of the target person H1 is evaluated by only the terminal device 30 without via the server device 20.

The terminal device 30 may include the voice acquiring unit 13, and the processing unit 34 of the terminal device 30 may have the functions of the information generating unit F1 and the start command unit F2.

Alternatively, the terminal device 30 may be the store device 10.

(3.4) Other Variation

In one variation, the store device 10 may include an accepting unit of accepting an operation about whether or not the pay information is required to be transmitted to the server device 20. The store device 10 may transmit, only when the salesperson of the store 1 operates the accepting unit, the pay information to the server device 20, for example.

In one variation, the store 1 is not limited to a retail store, but may be a virtual store. In this case, for example, the phone or the personal computer operated by the customer (target person H1) may transmit the voice data of the target person H1 to the server device 20 in accordance with the acquisition command received from the server device 20.

In one variation, the determining unit F12 may allow the evaluating unit F14 to evaluate the cognitive function of the target person H1, regardless of the contents of the pay information. That is to say, the determining unit F12 may determine, simply by using the acquisition of the pay information as a trigger, whether or not the evaluation for the cognitive function of the target person H1 by the evaluating unit F14 is required.

In one variation, the biological information (to be used by the evaluating unit F14 for evaluating the cognitive function) is not limited to the voice of the target person H1. The biological information (to be used by the evaluating unit F14 for evaluating the cognitive function) may be information relating to an eyeball movement of the target person H1, or information relating to walking of the target person H1, which can be acquired by an imaging unit (e.g., a camera). The imaging unit may be provided for the store device 10 or the information terminal carried by the target person H1, for example.

In one variation, the information acquiring unit F11 may receive the pay information after the settlement processing in the store device 10 is completed. In this case, the determining unit F12 determines, at an appropriate time point after the completion of the settlement processing, whether or not the evaluation by the evaluating unit F14 is required. When the determining unit F12 determines that the evaluation should be required, the biological information acquiring unit F13 allows the information terminal carried by the target person H1 to acquire the biological information of the target person H1. The evaluating unit F14 evaluates the cognitive function of the target person H1, using the biological information acquired by the information terminal. In this case, the present system cannot prevent the target person H1 from making unnecessary purchases, but can cancel the purchases made.

(4) Recapitulation

As can be seen from the foregoing description, an evaluation system (100) according to a first aspect includes an information acquiring unit (F11), an evaluating unit (F14), and a determining unit (F12). The information acquiring unit (F11) is configured to acquire pay information relating to a consideration which a target person (H1) should pay for reception of service. The evaluating unit (F14) is configured to evaluate a cognitive function of the target person (H1). The determining unit (F12) is configured to determine, by using acquiring of the pay information as a trigger, whether or not an evaluation for the cognitive function of the target person (H1) by the evaluating unit (F14) is required.

According to this aspect, determining of the cognitive function of the target person (H1) is executed by using acquiring of the pay information as a trigger. Consequently, this aspect can realize improving convenience.

An evaluation system (100) according to a second aspect, which may be implemented in conjunction with the first aspect, further includes an evaluation result recording unit (F15). The evaluation result recording unit (F15) is configured to associate, with the pay information, an evaluation result relating to the cognitive function of the target person (H1), obtained by the evaluating unit (F14), and record the evaluation result associated with the pay information.

This aspect can realize further improving convenience.

An evaluation system (100) according to a third aspect, which may be implemented in conjunction with the first or the second aspect, further includes a notification unit (F16). The evaluating unit (F14) is configured to express the cognitive function of the target person (H1) by a numerical value that represents a deterioration degree of the cognitive function of the target person (H1). The notification unit (F16) is configured to notify at least one, selected from the target person (H1) oneself, a family of the target person (H1) and a guardian of the target person (H1), of cancel information for cancelling paying of the consideration, when the numerical value representing the deterioration degree of the cognitive function evaluated by the evaluating unit (F14) is greater than a prescribed threshold.

According to this aspect, the evaluation system can perform the procedures for cancelling the payment based on the evaluation result by the evaluating unit (F14), of the cognitive function (the ability to judge something) of the target person (H1). Consequently, this aspect can realize further improving convenience.

In an evaluation system (100) according to a fourth aspect, which may be implemented in conjunction with any one of the first to third aspects, the pay information includes information about an amount of money as the consideration.

According to this aspect, the determining unit (F12) can determine, based on the information about the amount of money, whether or not the evaluation for the cognitive function of the target person (H1) is required. Consequently, this aspect can improve reliability of determining whether or not the evaluation is required.

In an evaluation system (100) according to a fifth aspect, which may be implemented in conjunction with any one of the first to fourth aspects, the reception of service includes acquisition of two or more pieces of merchandise. The pay information includes information about a combination in the two or more pieces of merchandise acquired.

According to this aspect, the determining unit (F12) can determine, based on the information about the combination in the two or more pieces of merchandise, whether or not the evaluation for the cognitive function of the target person (H1) is required. Consequently, this aspect can improve reliability of determining whether or not the evaluation is required.

In an evaluation system (100) according to a sixth aspect, which may be implemented in conjunction with the fifth aspect, the pay information includes information about the number of the two or more pieces of merchandise acquired.

According to this aspect, the determining unit (F12) can determine, based on the information about the number of the two or more pieces of merchandise, whether or not the evaluation for the cognitive function of the target person (H1) is required. Consequently, this aspect can improve reliability of determining whether or not the evaluation is required.

In an evaluation system (100) according to a seventh aspect, which may be implemented in conjunction with any one of the first to sixth aspects, the determining unit (F12) is configured to determine, based on a history of the pay information within a prescribed time period, whether or not the evaluation by the evaluating unit (F14) is required.

According to this aspect, the determining unit (F12) can determine, based on the history of the pay information within the prescribed time period, whether or not the evaluation for the cognitive function of the target person (H1) is required. Consequently, this aspect can improve reliability of determining whether or not the evaluation is required.

In an evaluation system (100) according to an eighth aspect, which may be implemented in conjunction with any one of the first to seventh aspects, the determining unit (F12) is configured to determine, based on the pay information about paying at one time, whether or not the evaluation by the evaluating unit (F14) is required.

According to this aspect, the determining unit (F12) can determine, based on the pay information about paying at one time, whether or not the evaluation for the cognitive function of the target person (H1) is required. That is to say, the determining unit (F12) can determine whether or not the evaluation for the cognitive function is required every payment.

In an evaluation system (100) according to a ninth aspect, which may be implemented in conjunction with any one of the first to eighth aspects, the evaluating unit (F14) is configured to evaluate, based on biological information of the target person (H1), the cognitive function of the target person (H1).

This aspect can improve reliability of the evaluation result of the cognitive function by the evaluating unit (F14).

In an evaluation system (100) according to a tenth aspect, which may be implemented in conjunction with the ninth aspect, the biological information of the target person (H1) includes voice data as information about a voice emitted by the target person (H1).

This aspect can improve reliability of the evaluation result of the cognitive function by the evaluating unit (F14).

An evaluation system (100) according to an eleventh aspect, which may be implemented in conjunction with the tenth aspect, further includes a voice data acquiring unit (F131). The voice data acquiring unit (F131) is configured to acquire the voice data of the target person (H1), when the determining unit (F12) determines that the evaluation by the evaluating unit (F14) is required.

This aspect can improve reliability of the evaluation result of the cognitive function by the evaluating unit (F14).

An evaluation system (100) according to a twelfth aspect, which may be implemented in conjunction with the tenth or eleventh aspect, further includes a target specifying unit (F17). The target specifying unit (F17) is configured to specify the target person (H1) based on the voice data and voiceprint information as information about a voiceprint of the target person (H1) previously acquired.

According to this aspect, the target person (H1) can be specified. Consequently, this aspect can realize further improving convenience.

An evaluation method according to a thirteenth aspect includes an information acquiring processing, an evaluating processing, and a determining processing. The information acquiring processing includes acquiring pay information relating to a consideration which a target person (H1) should pay for reception of service. The evaluating processing includes evaluating a cognitive function of the target person (H1). The determining processing includes determining, by using acquiring of the pay information as a trigger, whether or not an evaluation for the cognitive function of the target person (H1) is required.

According to this aspect, determining of the cognitive function of the target person (H1) is executed by using acquiring of the pay information as a trigger. Consequently, this aspect can realize improving convenience.

A program according to a fourteenth aspect is designed to cause one or more processors to execute the evaluation method of the thirteenth aspect.

This aspect can realize improving convenience.

A server device (20) according to a fifteenth aspect includes an information acquiring unit (F11), an evaluating unit (F14), and a determining unit (F12). The information acquiring unit (F11) is configured to acquire pay information relating to a consideration which a target person (H1) should pay for reception of service. The evaluating unit (F14) is configured to evaluate a cognitive function of the target person (H1). The determining unit (F12) is configured to determine, by using acquiring of the pay information as a trigger, whether or not an evaluation for the cognitive function of the target person (H1) by the evaluating unit (F14) is required.

According to this aspect, the server device (20) determines the cognitive function of the target person (H1) by using acquiring of the pay information as a trigger. Consequently, this aspect can realize improving convenience.

A terminal device (30) according to a sixteenth aspect includes an information acquiring unit (F11), an evaluating unit (F14), and a determining unit (F12). The information acquiring unit (F11) is configured to acquire pay information relating to a consideration which a target person (H1) should pay for reception of service. The evaluating unit (F14) is configured to evaluate a cognitive function of the target person (H1). The determining unit (F12) is configured to determine, by using acquiring of the pay information as a trigger, whether or not an evaluation for the cognitive function of the target person (H1) by the evaluating unit (F14) is required.

According to this aspect, the terminal device (30) determines the cognitive function of the target person (H1) by using acquiring of the pay information as a trigger. Consequently, this aspect can realize improving convenience.

The evaluation system (100) according to the first aspect may include the notification unit (F16) according to the third aspect, instead of the information acquiring unit (F11) and the determining unit (F12). That is to say, the evaluation system (100) according to the seventeenth aspect may include the evaluating unit (F14) and the notification unit (F16). The evaluating unit (F14) evaluates the cognitive function of the target person (H1), and express the cognitive function of the target person (H1) by a numerical value that represents a deterioration degree of the cognitive function of the target person (H1). The notification unit (F16) notifies at least one, selected from the target person (H1) oneself, a family of the target person (H1) and a guardian of the target person (H1), of cancel information for cancelling paying of the consideration, when the numerical value representing the deterioration degree of the cognitive function evaluated by the evaluating unit (F14) is greater than a prescribed threshold.

According to this aspect, a person received the cancel information can perform the procedures for cancelling the payment. Consequently, this aspect can realize improving convenience.

REFERENCE SIGNS LIST

20 Server Device
30 Terminal Device
100 Evaluation System
F11 Information Acquiring Unit
F12 Determining Unit
F131 Voice Data Acquiring Unit
F14 Evaluating Unit
F15 Evaluation Result Recording Unit
F16 Notification Unit
F17 Target Specifying Unit
H1 Target Person

The invention claimed is:

1. A system, comprising:
a point-of-sales (POS) terminal comprising a microphone; and
a server comprising a processor, wherein:
the processor is programmed to:
   acquire pay information relating to a consideration which a target person should pay for reception of service or a purchase of merchandise from the POS terminal,
   determine, based on the pay information, whether evaluating a cognitive function of the target person is necessary,
   when it is determined that evaluating the cognitive function of the target person is necessary, cause the POS terminal to acquire voice data as information about a voice emitted by the target person using the microphone,
   evaluate, based on the voice data, the cognitive function of the target person, the cognitive function of the target person being expressed by a numerical value that represents a deterioration degree of the cognitive function of the target person,
   when the numerical value representing the deterioration degree of the cognitive function evaluated by the evaluating unit is greater than a prescribed threshold, perform at least one action of:
      notifying the POS terminal of sales caution information, or
      notifying a user terminal of cancel information including one or more selected from: the pay information; information about a time limit by which return of the merchandise is permitted; and information about procedures required for return of the merchandise,
the cognitive function is evaluated by using a feature quantity, which is obtained by processing the voice data, and
the feature quantity includes at least one of (i) at least one of a first formant frequency or a second formant frequency of a vowel sound included in the voice data, (ii) a difference between a sound pressure of a consonant sound and a sound pressure of a vowel sound succeeding to the consonant sound, or (iii) a variation in differences, each of which is between a sound pressure of each of consonant sounds and a sound pressure of a vowel sound succeeding to a corresponding consonant sound, of vowel sounds.

2. A method, comprising:
acquiring, by a processor, pay information relating to a consideration which a target person should pay for reception of service or a purchase of merchandise from a point-of-sales (POS) terminal;
determining, by the processor, whether evaluating a cognitive function of the target person is necessary, based on the pay information;
after it is determined that evaluating the cognitive function of the target person is necessary, causing, by the processor, the POS terminal to acquire voice data as information about a voice emitted by the target person using the microphone;
evaluating, by the processor, the cognitive function of the target person based on the voice data, the cognitive function of the target person being expressed by a numerical value that represents a deterioration degree of the cognitive function of the target person; and
when the processor determines that numerical value representing the deterioration degree of the cognitive function evaluated by the evaluating unit is greater than a prescribed threshold, performing, at least one action of:
   notifying the POS terminal of sales caution information, or
   notifying a user terminal of cancel information including one or more selected from: the pay information; information about a time limit by which return of the merchandise is permitted; and information about procedures required for return of the merchandise,
wherein:
the cognitive function is evaluated by using a feature quantity, which is obtained by processing the voice data, and
the feature quantity includes at least one of (i) at least one of a first formant frequency or a second formant frequency of a vowel sound included in the voice data, (ii) a difference between a sound pressure of a consonant sound and a sound pressure of a vowel sound succeeding to the consonant sound, or (iii) a variation in differences, each of which is between a sound pressure of each of consonant sounds and a sound pressure of a vowel sound succeeding to a corresponding consonant sound, of vowel sounds.

* * * * *